United States Patent [19]

Hofmeister et al.

[11] 4,073,900
[45] Feb. 14, 1978

[54] 11 β-FLUOROPREGNENES

[75] Inventors: Helmut Hofmeister; Henry Laurent; Rudolf Wiechert; Klaus Annen; Hermann Steinbeck, all of Berlin, Germany

[73] Assignee: Schering Aktiengesellschaft, Berlin and Bergkamen, Germany

[21] Appl. No.: 734,012

[22] Filed: Oct. 19, 1976

[30] Foreign Application Priority Data

Oct. 22, 1975 Germany .......................... 2547687

[51] Int. Cl.² .................................... C07J 7/00
[52] U.S. Cl. ........................ 424/243; 260/397.45
[58] Field of Search .............................. 260/397.45

[56] References Cited

U.S. PATENT DOCUMENTS 3,636,011 1/1972 Phillipps et al. ................. 260/397.3

Primary Examiner—Elbert L. Roberts
Attorney, Agent, or Firm—Millen & White

[57] ABSTRACT

11β-Fluoropregnenes of the formula

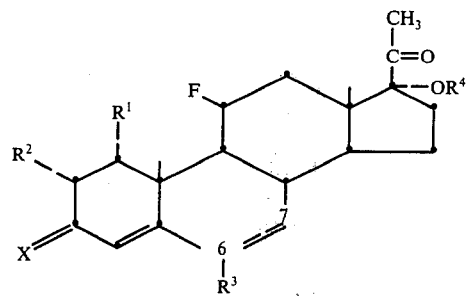

wherein
  6═══7 is a single or double bond,
  $R_1$ and $R_2$ each are H or collectively $CH_2$ or a single bond;
  $R_3$ is H or, when 6═══7 is a double bond, H, F or Cl,
  X or O or $HOR_4$ and
  $R_4$ is H or acyl, strong progestational activity and only weak antiandrogenic activity.

14 Claims, No Drawings

11 BETA-FLUOROPREGNENES

BACKGROUND OF THE INVENTION

This invention relates to novel 11β-fluoropregnenes.

SUMMARY OF THE INVENTION

In a composition aspect, this invention relates to novel 11β-fluoropregnenes of the general Formula I

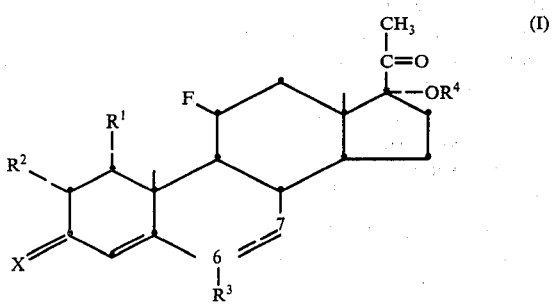

wherein

6====7 is a single or double bond between the C-6 and C-7 carbon atoms, $R_1$ and $R_2$ each are a hydrogen atom or collectively methylene or another carbon-carbon bond between the C-1 and C-2 carbon atoms, $R_3$ is a hydrogen atom or, when 6====7 is a double bond, a hydrogen, fluorine or chlorine atom, X is an oxygen atom or $H,OR_4$, and $R_4$ is a hydrogen atom or acyl.

In another composition aspect, this invention relates to pharmaceutical compositions comprising a novel 11β-fluoropregnene of this invention.

In process aspects, this invention relates to methods of making and of using the novel 11β-fluoropregnenes of this invention.

DETAILED DISCUSSION

Examples of contemplated as classes of compounds within the scope of Formula I are those wherein:
a. X is O;
b. 6====7 is a double bond;
c. 6====7 is a double bond and $R_3$ is Cl;
d. $R_1$ and $R_2$ collectively are a double bond, including each of (a), (b) and (c);
e. $R_1$ and $R_2$ collectively are methylene, including each of (a), (b), and (c);
f. $R_1$ and $R_2$ each are H, including each of (a), (b), and (c);
g. $R_4$ at the 17-position is H, including each of (a), (b), (c), (d), (e) and f); (f);
h. $R_4$ at the 17-position is alkanoyl of 1-7 carbon atoms, including each of (a), (b), (c), (d), (e), and (f).

Suitable $R_4$ acyl groups including physiologically acceptable acyl radicals of all acids conventionally employed for the esterification of steroid alcohols, particularly of organic carboxylic acids.

Preferred $R_4$ acyl groups are those of hydrocarbon carboxylic acids of 1-11, preferably 1-7 carbon atoms, and more preferably alkanoic acids, e.g., formic acid, acetic acid, propionic acid, butyric acid, isobutyric acid, valeric acid, isovaleric acid, caproic acid, enanthic acid, caprylic acid, pelargonic acid, capric acid, undecylic acid, trimethylacetic acid, diethylacetic acid, tert.-butylacetic acid, cyclopentylacetic acid, β-cyclopentyl-propionic acid, cyclohexylacetic acid, and β-cyclohexylpropionic acid. Contemplated as equivalents of these preferred acyl groups are all other acyl groups of carboxylic acids of the aliphatic, alicyclic, aromatic, hydroaromatic, or heterocyclic series, including both saturated or unsaturated acids, mono- or polybasic acids and/or acids substituted in the usual manner, e.g., by alkyl, hydroxy, alkoxy, oxo, amino, and/or halogen, e.g., mono-, di-, and trichloroacetic acid, aminoacetic acid, diethylaminoacetic acid, piperidinoacetic acid, morpholinoacetic acid, lactic acid, succinic acid, adipic acid and benzoic acid.

The novel 11β-fluoropregnenes possess valuable pharmacological properties. They possess surprisingly strong progestational activity with a minor antiandrogenic side effect. For example, 17-acetoxy-6-chloro-11β-fluoro-1α,2α-methylene-4,6-pregnadiene-3,20-dione (A) of the present invention proved to be superior, in the customary Clauberg and antiandrogen tests, to the conventional 17-acetoxy-6-chloro-1α,2α-methylene-4,6-pregnadiene-3,20-dione (B).

The antiandrogenic activity was tested on male castrated rats weighing about 100 g. Starting with 1 week after castration, the test compound was administered in staggered doses subcutaneously over a period of 7 days. Over the same time period, the animals received daily 0.1 mg. of testosterone propionate subcutaneously. On the eighth day, the animals were sacrificed, and the weights of the seminal vesicles were determined. As the $ED_{50}$, the daily dosage was determined which reduced the organ weight caused solely by testosterone propionate to one-half.

For the progestational effect, the McPhail values were determined in the usual Clauberg test after oral administration to infantile female rabbits. The minimum amount required to achieve a positive effect is expressed by the McPhail value of 1.5.

The results are compiled in the following table:

TABLE

| Compound | Progestational Activity Dose [mg.] | McPhail | Antiandrogenic Activity $ED_{50}$ Seminal Vesicle [mg.] |
|---|---|---|---|
| A 17-Acetoxy-6-chloro-11β-fluoro-1 α, 2α-methylene-4,6-pregnadiene-3,20-dione | 0.01<br>0.003<br>0.001 | 3.4<br>2.0<br>1.1 | 0.3 – 1.0 |
| B 17-Acetoxy-6-chloro-1 α, 2α-methylene-4,6-pregnadiene-3,20-dione | 0.01<br>0.003<br>0.001 | 2.9<br>1.5<br>1.0 | 0.1 – 0.3 |

It can be seen from the above data that the threshold dose (McPhail 1.5) for the progestational activity is, in case of the 11-fluoro compound (a) of this invention between 0.001 and 0.003 mg. and in case of the corresponding desfluoro compound (B), 0.003 mg. Moreover, Compound A of this invention has the advantage that it is antiandrogenically less active than the known compound B.

Due to their strong progestational activity, the 11β-fluoropregnenes of this invention are therapeutically very valuable compounds. They can be employed, for example, in a conventional manner in contraceptive preparations as the progestational component in combination with an estrogen-active hormone component, such as, for example, ethynylestradiol, or as the sole effective component. They can also be used in preparations for the treatment of gynecological disturbances.

For their use, the novel compounds are processes together with the additives, carrier materials, and flavor-ameliorating agents customary in galenic pharmacy into the customary forms of medicinal agents in accordance with conventional methods. Especially suitable for oral application are tablets, dragees, capsules, pills, suspensions, or solutions. For parenteral application, particularly suitable are oily solutions, e.g., sesame oil or castor oil solutions, which optionally can contain additionally a diluent, such as, for example, benzyl benzoate or benzyl alcohol. The concentration of the active agent is dependent on the form of application. Thus, for example, tablets for oral administration preferably contain 0.5 – 5.0 mg. of a compound of Formula I, and solutions for parenteral application contain preferably 1–200 mg. thereof per 1 ml. of solution.

The dosage of the agents of this invention can vary with the form and purpose of administration. For example, the daily contraceptive dose for fertile females upon oral ingestion is 0.5 – 5 mg.

In a process aspect, this invention relates to a process for the production of 11β-fluoropregnenes of general Formula I which comprises dehalogenating a 9-halo-11β-fluoropregnene of general Formula II

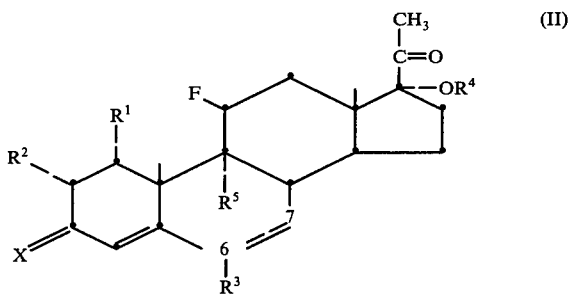

wherein $R_1$, $R_2$, $R_3$, X, $R_4$, as well as $C_6\!=\!=\!=\!C_7$ have the values given above and $R_5$ is chlorine or bromine, and optionally thereafter, depending on the desired final value for $R_1$ through $R_4$ and $C_6\!=\!=\!=\!C_7$, introducing one or more of a double bond in the 1- and/or 6-position, introducing a methylene group in the 1α,2α-position, introducing a fluorine or chlorine atom in the 6-position, reducing the 3-keto group, esterifying a free hydroxy group and hydrolyzing an esterified hydroxy group.

The dehalogenation of the halogen atom $R_5$ in the 9α-position can be accomplished with trialkyl- or triaryltin hydrides. The dehalogenation is suitable conducted by dissolving the starting steroid in a suitable solvent and adding the trialkyl- or triaryltin hydride thereto.

Examples of suitable trialkyltin hydrides are trimethyltin hydride, triethyltin hydride, and tributyltin hydride, the latter being preferred since it can be handled relatively simply.

Examples of suitable triaryltin hydrides are the tin hydrides of the mononuclear aromatics, such as alkyl($C_1$–$C_4$)-phenyl-, phenylalkyl($C_1$–$C_4$)-tin hydrides wherein the alkyl or phenyl residue can be in any desired position, and triphenyltin hydride, the latter being preferred.

The reaction is preferably conducted in the presence of a radical-forming agent, but this does not exclude the possibility of effecting the reaction of this invention even without such an agent, in which case longer reaction times may be necessary. Examples of suitable radical-forming agents are azobisisobutyronitrile and di-tert.-butyl peroxide. The reaction can also be conducted under UV irradiation.

The dehalogenation can also be conducted by forming the trialkyltin hydride only during the reaction of this invention. For this purpose, the corresponding trialkyltin oxide and polymethylsiloxane are added to the dissolved starting steroid. The advantage of this mode of operation is that readily decomposable trialkyltin hydrides need not be isolated beforehand.

Suitable solvents for the process of this invention are those which are inert with respect to the reactants, e.g., acyclic ethers, such as diethyl ether or glycol ether, cyclic ethers, such as tetrahydrofuran or dioxane, and hydrocarbons, such as hexane or benzene. Also suitable are alcohols, such as ethanol or glycol, and nitriles, such as acetonitrile.

The dehalogenation is suitably conducted at about room temperature. However, the process can also be accomplished at temperatures above room temperature, the upper temperature limit being the boiling point of the reaction mixture. The reaction also takes place at temperatures of below room temperature, but in such a case the reaction times may be very long.

The conductance of one or more of the optional measures takes place according to methods known to those skilled in the art. For the subsequent introduction of the double bonds in the 6,7- and/or 1,2-position, various methods can be selected.

An example for the introduction of the $\Delta^6$-double bond is the reaction with chloranil or the bromination with N-bromosuccinimide amd the subsequent splitting off of hydrogen bromide with lithium halide and an alkali metal carbonate.

For the introduction of the $\Delta^1$-double bond, suitable are the reaction with 2,3-dichloro-5,6-dicyano-1,4-benzoquinone, the dehydrogenation with a selenium compound, e.g., selenium dioxide or selenous acid, and microbiological $\Delta^1$-dehydrogenation.

For the simultaneous introduction of $\Delta^1$- and $\Delta^6$-double bonds, it is possible to employ the reaction with chloranil as well as bromination with bromine to the 2,6-derivative, followed by splitting off of hydrogen bromide with lithium halide and an alkali carbonate.

The introduction of the methylene group into the $\Delta^{1,4,6}$-3-ketone is achieved in a conventional manner, e.g., by reacting 1 molar equivalent of dimethyl methylenesulfonium oxide at temperatures of between −40° and −100° C., preferably at room temperature, with the unsaturated ketone. Dimethyl methylenesulfonium oxide can be liberated in the reaction mixture from trimethylsulfoxonium salts, e.g., halogenides, perchlorates, and methyl sulfates, with anhydrous bases, such as sodium hydride, sodium or potassium hydroxide or alcoholate, in aprotic solvents. A further possibility for the introduction of the methylene group is by reacting the $\Delta^{1,4,6}$-3-ketone with diazomethane with a subsequent thermal or catalytic splitting of the thus-formed 1′,2′-pyrazolino steroid.

To introduce a fluorine or chlorine atom in the 6-position, the $\Delta^{4,6}$-3-ketone is first converted into the 6,7-epoxide by treatment with a peracid, e.g., m-chloroperbenzoic acid. The 6,7-epoxide is then reacted with the corresponding hydrohalic acid. The reaction is conducted in an organic acid as the solvent, preferably in glacial acetic acid. Under these reaction conditions, water is split off from the primarily obtained 7-hydroxy-6-chloro(fluoro)-steroid, with elimination of the 7-hydroxy group and introduction of the $\Delta^6$-double bond. If the 1α,2α-methylene group is present, the cyclopropane ring is likewise split by hydrogen halide addition. The thus-obtained 1α-halomethyl compound can be reconverted into the 1α,2α-methylene compound by treatment with an inorganic or organic base to split off hydrogen halide.

The 3-keto group can be reduced by treatment with a complex metal hydride. Examples of suitable complex metal hydrides are sodium borohydride, lithium aluminum hydride, and lithium tri-tert.-butoxyakluminohydride. The process is advantageously carried out with sodium borohydride in a mixture of an alcohol, for example methanol, and water in the presence of an inorganic base.

The esterification is conducted in the usual manner with an acid derivative in the presence of an acidic or alkaline catalyst, e.g., by the reaction with an acid anhydride in the presence of p-toluenesulfonic acid at room temperature and the reaction with an acid anhydride in the presence of a tertiary amine under heating at about 30°–120° C.

Suitable for the hydrolysis is the reaction of the esters with alkali metal carbonates or hydroxides on an aqueous-alcoholic solution, optionally at an elevated temperature.

The preparation of the 9-halo-11β-fluoropregnenes utilized as starting compounds of general Formula II will be described by the use of the following compounds as examples:

17-acetoxy-9-bromo-11β-fluoro-4-pregnene-3,20-dione (A),
17-acetoxy-9-bromo-6-chloro-11β-fluoro-4,6-pregnadiene-3,20-dione (B), and
17-acetoxy-9-bromo-6-chloro-11β-fluoro-1α,2α-methylene-4,6-pregnadiene-3,20-dione (C).

A:
17-Acetoxy-9-bromo-11β-fluoro-4-pregnene-3,20-dione

At −78° C., 20 ml. of hydrogen fluoride is combined with 8 ml. of dimethylformamide, and 6 g. of 17-acetoxy-4,9(11)-pregnadiene-3,20-dione (J. Org. Chem. 26 [1961]: 866) and 4 g. of N-bromosuccinimide are added to the reaction mixture. The latter is allowed to stand for 3 hours at −30° C. and then introduced into a mixture of water, ice, and a 25% ammonia solution. The precipitate is filtered off, washed with water, taken up in ethyl acetate, and dried over sodium sulfate. After chromatography of the crude product on silica gel with 19-21.6% acetone/hexane, the yield is 3.0 g. of 17-acetoxy-9-bromo-11β-fluoro-4-pregnene-3,20-dione; m.p. 180°–182° C. (under decomposition).

B:
17-Acetoxy-9-bromo-6-chloro-11β-fluoro-4,6-pregnadiene-3,20-dione

At 80° C., 12.2 g. of 17-acetoxy-6-chloro-11β-hydroxy-4,6-pregnadiene-3,20-dione (DAS [German Published Application] 1,543,462) is agitated for 2.5 hours in 100 ml. of dimethylformamide, 40 ml. of pyridine, and 10 ml. of mesyl chloride. The reaction solution is stirred into ice water. The thus-precipitated product is vacuum-filtered, washed with water, taken up in ethyl acetate and dried over sodium sulfate. The crude product is chromatographed on silica gel with 7–9% acetone/methylene chloride, thus obtaining 7.0 g. of 17-acetoxy-6-chloro-4,6,9(11)-pregnatriene-3,20-dione; m.p. 211°–212° C. (under decomposition) from acetone/hexane.

At −30° C., 6.0 g. of 17-acetoxy-6-chloro-4,6,9(11)-pregnatriene-3,20-dione and 6 g. of N-bromosuccinimide are added in succession to 30 ml. of a 70% solution of hydrogen fluoride in pyridine. After 1.5 hours, the reaction solution is introduced into a mixture of ice water and a 25% ammonia solution. The precipitate is vacuum-filtered, washed with water, dissolved in ethyl acetate, and dried over sodium sulfate, thus producing 5.7 g. of 17-acetoxy-9-bromo-6-chloro-11β-fluoro-4,6-pregnadiene-3,20-dione.

C:
17-Acetoxy-9-bromo-6-chloro-11β-fluoro-1α,2α-methylene-4,6-pregnadiene-3,20-dione At 80° C., 2.7 g. of 17-acetoxy-6-chloro-11β-hydroxy-1α,2α-methylene-4,6-pregnadiene-3,20-dione (DAS 2,047,071) is agitated for 2 hours in 30 ml. of dimethylformamide, 15 ml. of pyridine, and 2.5 ml. of mesyl chloride. The solution is introduced into ice water. The thus-precipitated product is vacuum-filtered, washed with water, taken up in ethyl acetate, and dried over sodium sulfate. The crude product is recrystallized from acetone/hexane. Yield: 1.8 g. of 17-acetoxy-6-chloro-1α,2α-methylene-4,6,9(11)-pregnatriene-3,20-dione; m.p. 187°–188° C. (under decomposition) from acetone/hexane. UV: $\epsilon_{281} = 16,700$.

At −30° C., 1.5 g. of 17-acetoxy-6-chloro-1α,2α-methylene-4,6,9(11)-pregnatriene-3,20-dione and 1.5 g. of N-bromosuccinimide are added in succession to 7.5 ml. of a 70% solution of hydrogen fluoride in pyridine. After 1.5 hours, the solution is introduced into a mixture of ice water and 25% ammonia solution. The thus-precipitated product is vacuum-filtered, washed with water, dissolved in ethyl acetate, and dried over sodium sulfate. The crude product is recrystallized from acetone/hexane. Yield: 836 mg. of 17-acetoxy-9-bromo-6-chloro-11β-fluoro-1α,2α-methylene-4,6-pregnadiene-3,20 -dione; m.p. 189°–191° C. (under decomposition). UV: $\epsilon_{283} = 13,400$.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLE 1

3.6 g. of 17-acetoxy-9-bromo-11β-fluoro-4-pregnene-3,20-dione is agitated in 70 ml. of tetrahydrofuran at room temperature with 9.3 ml. of tributyltin hydride and 10 mg. of α,3α'-azobisisobutyronitrile. After 5 hours, the solution is concentrated under vacuum, and the residue is washed out repeatedly with hexane. After the crude product has been chromatographed on silica gel with 45–60% ethyl acetate/hexane, the yield is 1.1 g. of 17-acetoxy-11β-fluoro-4-pregnene-3,20-dione; m.p. 245°–246° C. from acetone/hexane. UV: $\epsilon_{239} = 16,700$.

EXAMPLE 2

One gram of 17-acetoxy-11β-fluoro-4-pregnene-3,20-dione is combined in a solvent mixture of 6 ml. of ethylene chloride and 10 ml. of tert.-butanol with 1.5 g. of chloranil and 10 mg. of p-toluenesulfonic acid. The mixture is heated for 6 hours under reflux. Then, the mixture is filtered off from the chloranil and the precipitate washed with ethyl acetate and ether. The filtrate is diluted with ether and combined repeatedly with 2N NaOH solution. The solution is then washed neutral with water and dried. After chromatography of the crude product on silica gel with 14–17% acetone/hexane, 344 mg. of 17-acetoxy-11β-fluoro-4,6-pregnadiene-3,20-dione is obtained; m.p. 220°–222° C. from acetone/hexane. UV: $\epsilon_{280} = 26,500$.

EXAMPLE 3

A solution of 1.2 g. of m-chloroperbenzoic acid in 5 ml. of tert.-butanol and 1 ml. of ethylene chloride is added to 600 mg. of 17-acetoxy-11β-fluoro-4,6-pregnadiene-3,20-dione in 25 ml. of ethylene chloride. The mixture is stirred for 21 hours at room temperature, diluted with ethyl acetate, washed in succession with sodium bisulfite solution and water, and dried over sodium sulfate. After the crude product has been chromatographed on silica gel with 45–55% ethyl acetate/hexane, the yield is 240 mg. of 17-acetoxy-6α,7α-epoxy-11β-fluoro-4-pregnene-3,20-dione [m.p. 222°–224° C. (under decomposition) from acetone/hexane. UV: $\epsilon_{238} = 13,600$.]

500 mg. of this epoxide is saturated with gaseous hydrogen chloride in 25 ml. of glacial acetic acid under ice cooling. The solution is allowed to stand for 24 hours at room temperature and then poured into ice water. The thus-precipitated product is vacuum-filtered, washed with water, taken up in ethyl acetate, and dried over sodium sulfate. The crude product is purified by preparative layer chromatography (eluent: ether/chloroform 8 + 2). After recrystallization from acetone/hexane, the yield is 207 mg. of 17-acetoxy-6-chloro-11β-fluoro-4,6-pregnadiene-3,20-dione; m.p. 235°–236° C. UV: $\epsilon_{283} = 20,300$.

EXAMPLE 4

Under nitrogen, 5.7 g. of 17-acetoxy-9-bromo-6-chloro-11β-fluoro-4,6-pregnadiene-3,20-dione is agitated for 5 days at room temperature in 140 ml. of tetrahydrofuran with 20 ml. of tributyltin hydride and 10 mg. of α,α'-azobisisobutyronitrile. The solution is evaporated under vacuum. The crude product is chromatographed on silica gel with 13-15% acetone/hexane, thus obtaining 1.0 g. of 17-acetoxy-6-chloro-11β-fluoro-4,6-pregnadiene-3,20-dione; m.p. 230°–233° C. from acetone/hexane. UV: $\epsilon_{283} = 19,200$.

EXAMPLE 5

10.0 g. of 17-acetoxy-9-bromo-6-chloro-11β-fluoro-1α,2α-methylene-4,6-pregnadiene-3,20-dione in 200 ml. of tetrahydrofuran is agitated under nitrogen at room temperature with 40 ml. of tributyltin hydride and 20 mg. of α,α'-azobisisobutyronitrile. After 4 hours, the solution is concentrated under vacuum. The crude product is chromatographed on silica gel. With 3.5 – 7% acetone/methylene chloride, 5.7 g. of 17-acetoxy-6-chloro-11β-fluoro-1α,2α-methylene-4,6-pregnadiene-3,20-dione is eluted; m.p. 253°–254° C. from acetone/hexane. UV: $\epsilon_{282} = 16,800$.

EXAMPLE 6

As described in Example 5, 2.1 g. of 17-acetoxy-9-bromo-6-chloro-11β-fluoro-1α,2α-methylene-4,6-pregnadiene-3,20-dione is reacted in 40 ml. of tetrahydrofuran with 8 ml. of triphenyltin hydride and 5 mg. of α,α'-azobisisobutyronitrile. After 2 hours, the solution is concentrated to dryness under vacuum. The crude product is chromatographed on silica gel with 3 – 6.5% acetone/methylene chloride. Yield: 1.2 g. of 17-acetoxy-6-chloro-11β-fluoro-1α,2α-methylene-4,6-pregnadiene-3,20-dione, m.p. 250°–252° C. from acetone/hexane. UV: $\epsilon_{282} = 16,300$.

EXAMPLE 7

At room temperature, 2.4 g. of 17-acetoxy-11β-fluoro-4-pregnene-3,20-dione is agitated in a mixture of 60 ml. of methanol and 15 ml. of methylene chloride with 20 ml. of a 1N sodium hydroxide solution for 10 hours. The solution is extensively concentrated under vacuum, the reaction product is taken up in methylene chloride and dried over sodium sulfate. The crude product is chromatographed on silica gel with 20–25% acetone/hexane, thus obtaining 1.4 g. of 11β-fluoro-17-hydroxy-4-pregnene-3,20-dione; m.p. 210°–215° C. from acetone/hexane. UV: $\epsilon_{239} = 15,900$.

EXAMPLE 8

For 2 days, 225 mg. of 11β-fluoro-17-hydroxy-4-pregnene-3,20-dione is heated under nitrogen and reflux in 2 ml. of pyridine with 1 ml. of propionic acid anhydride. The solution is introduced into ice water which contains sulfuric acid, and the reaction product is extracted with methylene chloride. The solution is dried over sodium sulfate. After purification of the crude product by preparative layer chromatography (eluent: ether/chloroform 8 + 2), the yield is 110 mg. of 11β-fluoro-17-propionyloxy-4-pregnene-3,20-dione as a foamy product. UV: $\epsilon_{239} = 15,600$.

EXAMPLE 9

As described in Example 8, 320 mg. of 11β-fluoro-17-hydroxy-4-pregnene-3,20-dione is heated for 3 days under reflux with 2 ml. of caproic acid anhydride in 4 ml. of pyridine. The solution is introduced into ice water. The reaction product is extracted from methylene chloride and dried over sodium sulfate. The crude product is purified by preparative layer chromatography (eluent: ether/chloroform 8 + 2), yielding 80 mg. of 11β-fluoro-17-hexanoyloxy-4-pregnene-3,20-dione as an oil. UV: $\epsilon_{239} = 15,800$.

By proceeding analogously to Example 9, but with the use of enanthic acid anhydride in place of caproic acid anhydride, 60 mg. of 11β-fluoro-17-heptanoyloxy-4-pregnene-3,20-dione is obtained.

EXAMPLE 10

4.6 g. of 17-acetoxy-11β-fluoro-4,6-pregnadiene-3,20-dione is refluxed for 12 hours in 40 ml. of benzene with 4.7 g. of 2,3-dichloro-5,6-dicyano-1,4-benzoquinone. The reaction mixture is diluted with ether and washed repeatedly in succession with 2N sodium hydroxide solution and water. The solution is dried over sodium sulfate. The crude product is chromatographed on silica gel with acetone/hexane, thus isolating 1.9 g. of 17-acetoxy-11β-fluoro-1,4,6-pregnatriene-3,20-dione as an oily product. UV: $\epsilon_{298} = 11,800$.

EXAMPLE 11

2.3 g. of 17-acetoxy-11β-fluoro-1,4,6-pregnatriene-3,20-dione in a mixture of 60 ml. of methanol and 20 ml. of methylene chloride is combined with 20 ml. of a 1N sodium hydroxide solution and agitated for 6 hours at room temperature. The solution is concentrated under vacuum; the reaction product is taken up in methylene chloride and dried over sodium sulfate, thus obtaining 1.8 g. of crude 11β-fluoro-17-hydroxy-1,4,6-pregnatriene-3,20-dione as a foamy product. UV: $\epsilon_{297} = 11,600$.

EXAMPLE 12

One gram of trimethylsulfoxonium iodide in 30 ml. of dimethyl sulfoxide is agitated under nitrogen for 30 minutes with 200 mg. of pulverized sodium hydroxide. Then, 1.6 g. of 11β-fluoro-17-hydroxy-1,4,6-pregnatriene-3,20-dione is added to the reaction mixture. After 4.5 hours, the reaction mixture is stirred into acetic ice/water. The precipitate is vacuum-filtered, taken up in methylene chloride, and dried over sodium sulfate. After chromatographing the crude product on silica gel with acetone/hexane, 1.4 g. of 11β-fluoro-17-hydroxy-1α,2α-methylene-4,6-pregnadiene-3,20-dione is obtained. UV: $\epsilon_{282} = 16,900$.

EXAMPLE 13

1.2 g. of 11β-fluoro-17-hydroxy-1α,2α-methylene-4,6-pregnadiene-3,20-dione in 15 ml. of glacial acetic acid is agitated at room temperature for 17 hours with 10 ml. of acetic anhydride and 800 mg. of p-toluenesulfonic acid. The reaction mixture is introduced into ice/water. The precipitate is vaccum-filtered, washed with water, taken up in methylene chloride, and dried, thus obtaining 820 mg. of 17-acetoxy-11β-fluoro-1α,2α-methylene-4,6-pregnadiene-3,20-dione. UV: $\epsilon_{282} = 17,100$.

EXAMPLE 14

A solution of 4.0 g. of m-chloroperbenzoic acid in 10 ml. of tert.-butanol is combined with 700 mg. of 17-acetoxy-11β-fluoro-1α,2α-methylene-4,6-pregnadiene-3,20-dione in 60 ml. of ethylene chloride. The solution is allowed to stand for 48 hours at room temperature, then diluted with ethyl acetate, and washed in succession with sodium bisulfite solution and water. Yield: 510 mg. of 17-acetoxy-6α,7α-epoxy-11β-fluoro-1α,2α-methylene-4-pregnene-3,20dione, which is introduced into 10 ml. of glacial acetic acid saturated with gaseous hydrogen chloride. After 22 hours, the solution is poured into ice/water. The thus-precipitated product is vacuum-filtered, washed with water, taken up in methylene chloride, and dried over sodium sulfate. The thus-produced crude 17-acetoxy-6-chloro-1α-chloromethyl-11β-fluoro-4,6-pregnadiene-3,20-dione (380 mg.) is agitated in 5 ml. of collidine for 6 hours at 140° C. After cooling, the solution is diluted with ether and washed repeatedly in succession with 2N hydrochloric acid and water. The ether phase is dried over sodium sulfate. The crude product is purified by preparative layer chromatography (system: ether/chloroform 8+2), thus obtaining 175 mg. of 17-acetoxy-6-chloro-11β-fluoro-1α,2α-methylene-4,6-pregnadiene-3,20-dione; m.p. 250°–252° C. UV: $\epsilon_{282} = 16,650$.

EXAMPLE 15

2.5 ml. of 0.3% sodium hydroxide solution and 1.1 g. of sodium borohydride are added to 800 mg. of 17-acetoxy-6-chloro-11β-fluoro-1α,2α-methylene-4,6-pregnadiene-3,20-dione in 40 ml. of methanol. The solution is agitated under nitrogen for 1.5 hours at room temperature, then diluted with ethyl acetate, washed neutral, dried over sodium sulfate, and concentrated under vacuum. The crude product is purified by preparative layer chriomatography (system: ether/chloroform 8+2), thus obtaining 360 mg. of 17-acetoxy-6-chloro-11β-fluoro-3β-hydroxy-1α,2α-methylene-4,6-pregnadien-20-one as a foamy product. UV: $\epsilon_{243} = 22,600$.

EXAMPLE 16

560 mg. of 17-acetoxy-6-chloro-11β-fluoro-4,6-pregnadiene-3,20-dione in 35 ml. of methanol is combined with 1.5 ml. of 0.3% sodium hydroxide solution and 900 mg. of sodium borohydride. The solution is stirred for 45 minutes at room temperature and then worked up as described in Example 15. The crude product is purified by preparative layer chromatography (system: ether/chloroform 8+2). Yield: 230 mg. of 17-acetoxy-6-chloro-11β-fluoro-3β-hydroxy-4,6-pregnadien-20-one in the form of an oil. UV: $\epsilon_{243} = 24,000$.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

EXAMPLE 17

| Dragee Composition (daily contraceptive dose for fertile females) | |
| --- | --- |
| 1.000 mg. | 17-acetoxy-6-chlor:11β-fluoro-1α, 2α-methylene-4,6-pregnadiene-3,20-dione |
| 0.050 mg. | 17α-ethynylestradiol |
| 30.950 mg. | lactose (DAB 6) (German Pharmacopoeia) |
| 18.425 mg. | corn starch (USP SVI) |
| 2.060 mg. | polyvinylpyrrolidone 25 |
| 0.010 mg. | methyl-p-hydroxybenzoate (methylparaben) |
| 0.005 mg. | propyl-p-hydroxybenzoate (propylparaben) |
| 2.500 mg. | talc |
| 55.000 mg. | total weight of the tablet which is made into a dragee with a weight of about 90 mg. with the usual sugar mixture |

What is claimed is:
1. An 11β-fluoropregnene of the formula

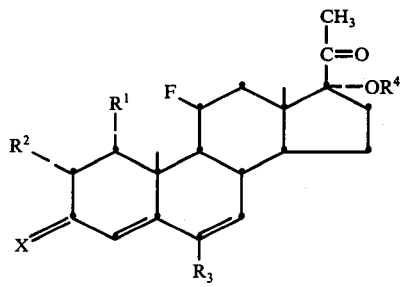

wherein $R_1$ and $R_2$ each are a hydrogen atom or collectively methylene or a carbon-carbon bond; $R_3$ is a hydrogen, fluorine or chlorine atom; X is an oxygen atom or H,$OR_4$, and $R_4$ is a hydrogen atom or the acyl radical of a hydrocarbon carboxylic acid of 1–11 carbon atoms.

2. 17-Acetoxy-11β-fluoro-4,6-pregnadiene-3,20-dione, a compound of claim 1.

3. 17-Acetoxy-6-chloro-11β-fluoro-4,6-pregnadiene-3,20-dione, a compound of claim 1.

4. 17-Acetoxy-6-chloro-11β-fluoro-1α,2α-methylene-4,6-pregnadiene-3,20-dione, a compound of claim 1.

5. 17-Acetoxy-11β-fluoro-1,4,6-pregnatriene-3,20-dione, a compound of claim 1.

6. 11β-Fluoro-17-hydroxy-1,4,6-pregnatriene-3,20-dione, a compound of claim 1.

7. 11β-Fluoro-17-hydroxy-1α,2α-methylene-4,6-pregnadiene-3,20-dione, a compound of claim 1.

8. 17-Acetoxy-11β-fluoro-1α,2α-methylene-4,6-pregnadiene-3,20-dione, a compound of claim 1.

9. 17-Acetoxy-6-chloro-11β-fluoro-3β-hydroxy-1α,2α-methylene-4,6-pregnadien-20-one, a compound of claim 1.

10. 17-Acetoxy-6-chloro-11β-fluoro-3β-hydroxy-4,6-pregnadien-20-one, a compound of claim 1.

11. A pharmaceutical composition comprising a progestationally effective amount per unit dosage of a compound of claim 1, in admixture with a pharmaceutically acceptable carrier.

12. A pharmaceutical composition adapted for oral injestion and comprising a contraceptively effective amount of a mixture of a compound of claim 1, and a pharmaceutically acceptable carrier.

13. A method of contraception which comprises administering daily orally to a fertile female a contraceptively effective amount of a compound of claim 1.

14. A process for the production of 11β-fluoropregnenes of claim 1, which comprises dehalogenating with a trialkyl - or triaryltin hydride a 9-halo-11β-fluoropregnene of the formula

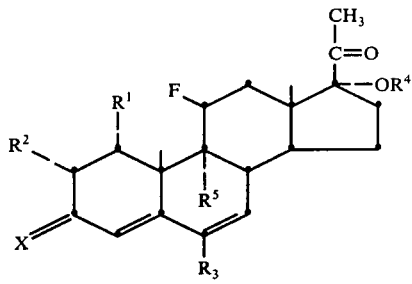

wherein $R_1$, $R_2$, $R_3$, X and $R_4$ have the values given above, and $R_5$ is chlorine or bromine.

* * * * *